US009908847B2

(12) United States Patent
Bonrath et al.

(10) Patent No.: US 9,908,847 B2
(45) Date of Patent: Mar. 6, 2018

(54) METHOD FOR PRODUCING SPECIFIC α,β-UNSATURATED ALDEHYDES BY REARRANGEMENT PROCESS

(71) Applicant: DSM IP ASSETS B.V., Heerlen (NL)

(72) Inventors: Werner Bonrath, Kaiseraugst (CH); Jan Schuetz, Kaiseraugst (CH); Thomas Netscher, Kaiseraugst (CH); Bettina Wuestenberg, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/518,383

(22) PCT Filed: Oct. 15, 2015

(86) PCT No.: PCT/EP2015/073877
§ 371 (c)(1),
(2) Date: Apr. 11, 2017

(87) PCT Pub. No.: WO2016/059155
PCT Pub. Date: Apr. 21, 2016

(65) Prior Publication Data
US 2017/0313655 A1    Nov. 2, 2017

(30) Foreign Application Priority Data
Oct. 16, 2014    (EP) .................................... 14189267

(51) Int. Cl.
C07C 45/00    (2006.01)
C07C 403/00   (2006.01)
C07C 403/14   (2006.01)

(52) U.S. Cl.
CPC .................................. *C07C 403/14* (2013.01)

(58) Field of Classification Search
CPC ........................... C07C 403/14; C07C 45/512
USPC .......................................................... 568/443
See application file for complete search history.

(56) References Cited

PUBLICATIONS

International Search Report for PCT/EP2015/073877, dated Jan. 21, 2016, 3 pages.
Written Opinion of the ISA for PCT/EP2015/073877, dated Jan. 21, 2016, 5 pages.
Wei et al., "A Novel Aldol Condensation Alternative: α,β-Unsaturated Aldehydes from 3-Hydroxy-1-alkynes via Dihydrodioxepins", Chemistry—A European Journal, vol. 4, No. 9, Sep. 4, 1998, pp. 1738-1743.
Clapperton et al., "The Acid-Catalyzed Rearrangement of Substituted Phenylethynylcarbinols and Styrylethynylcarbinol", Journal of the American Chemical Society, vol. 72, No. 6, Jun. 1, 1950, pp. 2501-2502.
Arens et al., "Synthesis of vitamin A", Recueil Des Travaux Chimiques Des Pays-Bas, vol. 68, No. 7, Sep. 2, 1949, pp. 604-608.
Ishikawa, "Synthesis of beta-ionylideneacetaldehyde", Chemical Abstracts, Jan. 15, 1968, XP002222823.

*Primary Examiner* — Sikarl Witherspoon
(74) *Attorney, Agent, or Firm* — Nixon & Vanderhye P.C.

(57) ABSTRACT

The present invention relates to an improved method for producing specific α,β-unsaturated aldehydes.

11 Claims, No Drawings

METHOD FOR PRODUCING SPECIFIC α,β-UNSATURATED ALDEHYDES BY REARRANGEMENT PROCESS

This application is the U.S. national phase of International Application No. PCT/EP2015/073877 filed 15 Oct. 2015, which designated the U.S. and claims priority to EP Patent Application No. 14189267.9 filed 16 Oct. 2014, the entire contents of each of which are hereby incorporated by reference.

The present invention relates to an improved method for producing specific α,β-unsaturated aldehydes.

The specific α,β-unsaturated aldehydes which are aimed to be produced are represented by the following formula (I)

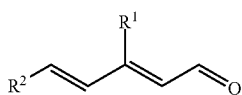

wherein
$R^1$ is a $C_1$-$C_4$-alkyl moiety, preferably —$CH_3$ or —$CH_2CH_3$, and
$R^2$ is

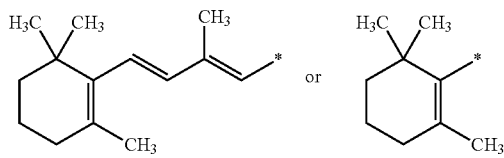

(the * is showing where the bond is localized).

These specific α,β-unsaturated aldehydes always have conjugated C—C-double bonds.

These specific α,β-unsaturated aldehydes are useful compounds. They can be used as such or they are useful intermediates to produce other compounds. For example compound (Ia)

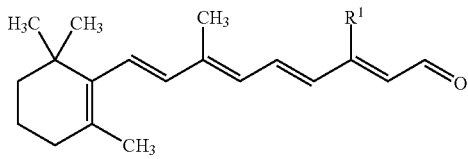

is used as an intermediate in the production of Vitamin A acetate (via a reduction followed by an acetylation).

Therefore due to the importance of such specific α,β-unsaturated aldehydes, there is always a need for improved methods of producing such compounds.

Now surprisingly, it was found that such specific α,β-unsaturated aldehydes having conjugated C—C-double bonds can be produced by a catalysed Meyer-Schuster rearrangement. The use of a Meyer-Schuster rearrangement to produce such compounds is not known.

The Meyer-Schuster rearrangement, which was published first in 1922 by Kurt Meyer and Kurt Schuster, is the chemical reaction described as an acid-catalyzed rearrangement of secondary and tertiary propargyl alcohols to α,β-unsaturated aldehydes.

The Meyer-Schuster rearrangement is usually carried out by using catalysts based on (transition) metals and/or metal oxides.

The goal of the present invention was to find an improved method for the production of compounds of formula (I).

Surprisingly it was found that a compound of formula (II)

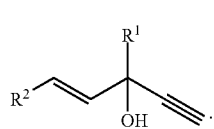

wherein $R^1$ and $R^2$ have the same meanings as defined in formula (I), can be used as starting material in a transition metal-based catalyzed Meyer-Schuster rearrangement to produce compounds of formula (I), wherein the transition metal is Cu and/or Ti.

Therefore the present invention relates to a process (P) for the production of compounds of formula (I)

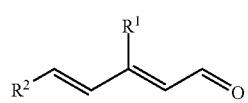

wherein
$R^1$ is a $C_1$-$C_4$-alkyl moiety, preferably —$CH_3$ or —$CH_2CH_3$, and
$R^2$ is

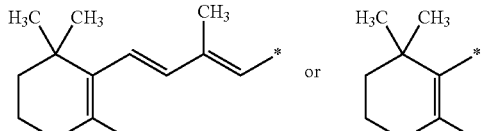

(the * is showing where the bond is localized)
by rearrangement of the compound of formula (II)

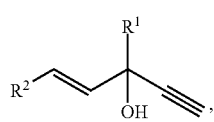

wherein $R^1$ and $R^2$ have the same meanings as in formula (I), characterized in that the process is carried out in the presence of at least one transition metal-based catalyst, wherein the transition metal is Cu and/or Ti.

It is not known from the prior art that such α,β-unsaturated aldehydes having conjugated C—C double bonds can be produced by this process.

The process according to the present invention is usually carried out as an one pot-reaction under mild conditions resulting in good selectivity and yield.

In a preferred embodiment of the present invention compounds of formula (IIa) or of formula (IIb)

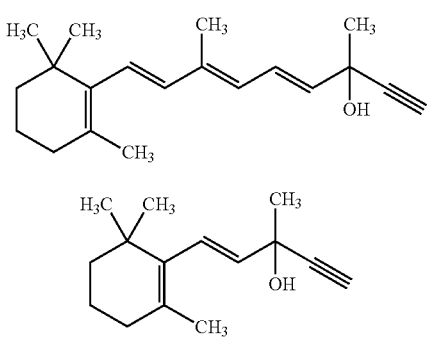

are used as starting material.

The corresponding products (when using compounds of formula (IIa) or of formula (IIb) as starting material) are those of formula (Ia) and of formula (Ib)

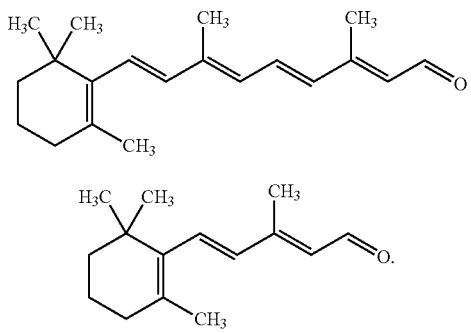

Therefore the present invention also relates to a process (P$_1$), which is process (P), wherein the compound of formula (II) is the compound of formula (IIa)

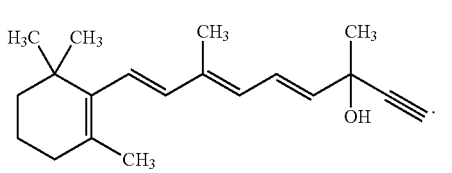

Therefore the present invention also relates to a process (P$_2$), which is process (P), wherein the compound of formula (II) is the compound of formula (IIb)

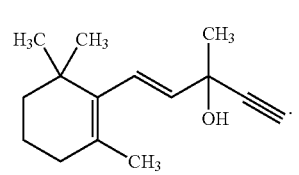

A transition metal-based catalyst is used (or a mixture of transition metal based catalysts) for the process according to the present invention, wherein the transition metal is Cu and/or Ti.

A preferred catalyst is one wherein a mixture of Cu and Ti is used, such as CuCl/Ti(O)(acac)$_2$. acac is the abbreviation of acetylacetonate.

The Cu:Ti ratio (mol-based) can vary. When using CuCl/Ti(O)(acac)$_2$, then the Cu:Ti ratio is 1:5-5:1, preferably CuCl:Ti(O)(acac)$_2$ ratio is 2:1.5.

The catalysts as described above are known from the prior art and can be produced as described therein.

Therefore the present invention also relates to a process (P$_3$), which is process (P), (P$_1$) or (P$_2$), wherein the transition metal based catalyst is a CuCl/Ti(O)(acac)$_2$ based catalyst.

The substrate (starting material) to catalyst ratio (mol-based) is usually from 5000:1 to 10:1, preferably from 1000:1 to 20:1.

Therefore the present invention also relates to a process (P$_4$), which is process (P), (P$_1$), (P$_2$) or (P$_3$), wherein the substrate to catalyst ratio (mol-based) is from 5000:1 to 10:1, preferably from 1000:1 to 20:1.

The process according to the present invention is a Meyer-Schuster rearrangement. Mild reaction conditions are used for the process according to the present invention.

Usually the process according to the present invention is carried out in at least one non polar or polar aprotic organic solvent.

All reactants are added together and mixed. The reaction mixture is heated to the temperature at which the transition metal-based catalytic rearrangement reaction occurs, to provide a resulting mixture.

As solvents there can be used in the scope of the present invention in general non polar or polar aprotic organic solvents, especially aliphatic, cyclic and aromatic hydrocarbons, such as, for example, $C_7$-$C_{10}$-alkanes, $C_5$-$C_7$-cycloalkanes, benzene, toluene and naphthalene as well as mixtures of such solvents with one another, e.g. paraffin oil (a mixture of saturated aliphatic hydrocarbons); as well as carboxylate esters, such as ethyl acetate.

The rearrangement according to present invention usually comprises (1) the rearrangement process is started with the addition of the starting material, the catalyst, the solvent as well as the organic acid having a pK value in the range of about 4.0 to about 6.5 (the sequence of adding these compounds is not of importance. Furthermore it is clear that it is also possible adding mixtures of each of the components as well.)

(2) and optionally afterwards the reaction mixture is acidified with an acid or a mixture of acids (such as i.e. sulphuric acid).

Therefore the present invention relates to a process (P$_5$), which is process (P), (P$_1$), (P$_2$), (P$_3$) or (P$_4$), characterized in that the rearrangement is carried out in at least one non polar or polar aprotic organic solvent.

Therefore the present invention also relates to a process (P$_5$'), which is process (P$_5$), wherein the non polar or polar aprotic organic solvent is chosen from the group consisting of aliphatic, cyclic and aromatic hydrocarbons (such as $C_7$-$C_{10}$-alkanes, $C_5$-$C_7$-cycloalkanes, benzene, toluene naphthalene, paraffin oil) and carboxylate esters (such as ethyl acetate).

The process according to the present invention is usually carried out at elevated temperatures. Usually above 50° C. A preferred range is 50° C. to 120° C., more preferred is a range from 60° C. to 100° C.

Therefore the present invention relates to a process (P$_6$), which is process (P), (P$_1$), (P$_2$), (P$_3$), (P$_4$), (P$_5$) or (P$_5$'), wherein the process is carried out at a reaction temperature of 50° C. to 120° C., preferably 60° C. to 100° C.

The products obtained by the process according to the present invention can be used as such or they can be used as intermediates for the production of other organic compounds. For example, the compound of formula (Ia) can be used in the production of Vitamin A acetate (via a reduction followed by an acetylation). The same applies for the compound of formula (Ib), which can also be used in the production of Vitamin A acetate (compound (IIa) is the product of an aldol condensation of compound of formula (Ib) followed by an ethynylation).

The following examples illustrate the invention further without limiting it. All percentages and parts, which are given, are related to the weight and the temperatures are given in ° C., when not otherwise stated.

EXAMPLES

Example 1: 3-Methyl-5-(2,6,6-trimethylcyclohex-1-enyl)penta-2,4-dienal (Compound of Formula (Ib))

8.74 mg of titanium(IV)-oxyacetylacetonate (0.03 mmol) and 4.08 mg of copper(I)-chloride (0.04 mmol) were added to a vial. The vial was sealed with a septum. 0.46 g of starting material (IIb, 2.00 mmol) in 4 ml of anhydrous toluene was added. The solution was stirred for 15 hours at 90° C., then cooled to 23° C. and stirred for another 3.5 hours. The solution was diluted with 15 ml of ethyl acetate and washed with 15 ml of diluted brine (20%). The layers were separated and the organic layer was washed with another 15 ml of diluted brine (20%). The aqueous layers were re-extracted with 15 ml of ethyl acetate. The combined organic layers were dried over sodium sulfate, filtered and concentrated under reduced pressure at 30° C. water-bath temperature. The product (Ib) was obtained as a dark brown oil in 26.12% purity and 27% yield (0.455 g).

Example 2: Retinal (Compound of Formula (Ia))

8.7 mg of titanium(IV)-oxyacetonylacetonate and 4.1 mg of copper(I)-chloride were added to a flask. A solution of 651.7 mg of starting material (IIa) in 4.0 ml of anhydrous toluene were added drop wise. The reaction mixture was heated to 85° C. in an oil bath under argon atmosphere. After 48 hours at 85° C. the dark brown suspension was cooled to 24° C. 15 ml of methylene chloride were added to the reaction mixture. The mixture was washed with 15 ml of semi-saturated NaHCO$_3$-solution and 15 ml of semi-saturated brine. The layers were separated and the aqueous layers were re-extracted with 15 ml of methylene chloride. The combined organic layers were dried over sodium sulfate, filtered and concentrated under reduced pressure at 30° C. water bath temperature. The product (Ia) was obtained as dark orange oil (707.1 mg).

The invention claimed is:
1. A process for producing a compound of formula (I):

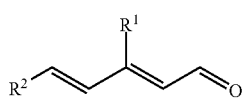
(I)

wherein R$^1$ is a C$_1$-C$_4$-alkyl moiety, and R$^2$ is

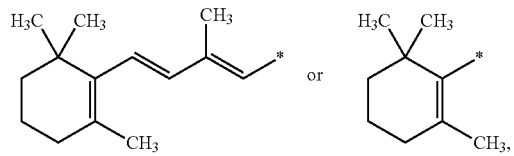

wherein the process comprises rearranging a compound of formula (II):

(II)

wherein R$^1$ and R$^2$ have the same meanings as in formula (I), in the presence of at least one Cu and/or Ti transition metal based catalyst.

2. The process according to claim 1, wherein the compound of formula (II) is a compound of formula (IIa):

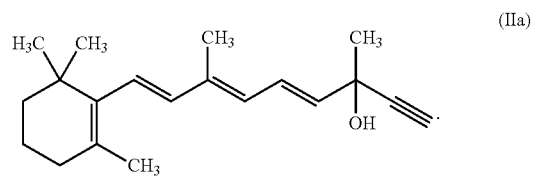 [SMILES: C#CC(C)(O)/C=C/C=C(C)/C=C/C1=C(C)CCCC1(C)C]
(IIa)

3. The process according to claim 1, wherein the compound of formula (II) is a compound of formula (IIb):

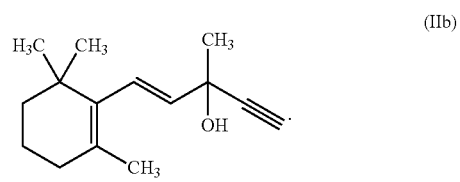 [SMILES: C#CC(C)(O)/C=C/C1=C(C)CCCC1(C)C]
(IIb)

4. The process according to claim 1, wherein the transition metal-based catalyst is a Cu/Ti-based catalyst.

5. The process according to claim 1, wherein the transition metal-based catalyst is CuCl/Ti(O)(acac)$_2$.

6. The process according to claim 1, wherein the transition metal-based catalyst has a mol-based substrate to catalyst ratio from 5000:1 to 10:1.

7. The process according to claim 1, wherein the process is carried out in at least one nonpolar or polar aprotic organic solvent.

8. The process according to claim 1, wherein the process is carried out at a reaction temperature of 50° C. to 120° C.

9. The process according to claim 8, wherein the reaction temperature is 60° C. to 100° C.

10. The process according to claim 1, wherein R$^1$ is —CH$_3$ or —CH$_2$CH$_3$.

11. The process according to claim 6, wherein the mol-based substrate to catalyst ratio is from 1000:1 to 20:1.

* * * * *